(12) United States Patent
Boas et al.

(10) Patent No.: US 9,265,460 B2
(45) Date of Patent: Feb. 23, 2016

(54) OPTICAL FIBER PROBE ARRANGEMENT FOR USE WITH X-RAY MAMMOGRAPHY

(71) Applicant: THE GENERAL HOSPITAL CORPORATION, Boston, MA (US)

(72) Inventors: David Boas, Winchester, MA (US); Stefan Carp, Revere, MA (US); Mark Martino, Cos cob, CT (US); Qianqian Fang, North Reading, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/517,398

(22) Filed: Oct. 17, 2014

(65) Prior Publication Data

US 2015/0110242 A1  Apr. 23, 2015

Related U.S. Application Data

(60) Provisional application No. 61/892,197, filed on Oct. 17, 2013.

(51) Int. Cl.
*G01J 5/00* (2006.01)
*A61B 6/04* (2006.01)
*A61B 5/00* (2006.01)
*A61B 6/00* (2006.01)

(52) U.S. Cl.
CPC ............. *A61B 5/4312* (2013.01); *A61B 5/0035* (2013.01); *A61B 5/0073* (2013.01); *A61B 5/0091* (2013.01); *A61B 6/502* (2013.01)

(58) Field of Classification Search
CPC ..................... G01J 5/00; A61B 6/04
See application file for complete search history.

(56) References Cited

U.S. PATENT DOCUMENTS

| 4,948,974 | A | * | 8/1990 | Nelson et al. | ............... 250/358.1 |
| 6,031,892 | A | * | 2/2000 | Karellas | ....................... 378/98.3 |
| 6,345,194 | B1 | * | 2/2002 | Nelson et al. | ................. 600/425 |

OTHER PUBLICATIONS

GLOBOCAN2008. "Estimated cancer Incidence, Mortality, Prevalence and Disability-adjusted life years (DALYs) Worldwide in 2008." Retrieved Oct. 1, 2013 http://globocan.iarc.
Berry, D. A., et al. (2005). "Effect of screening and adjuvant therapy on mortality from breast cancer." The New England journal of medicine 353(17): 1784-1792.
Chatterjee, Neal A., et al. (2012). "Racial Differences in Breast Cancer Stage at Diagnosis in the Mammography Era." American Journal of Public Health 103(1): 170-176.
Singletary, S. E. (2007). "Multidisciplinary frontiers in breast cancer management—A surgeon's perspective." Cancer 109(6): 1019-1029.

(Continued)

*Primary Examiner* — David Porta
*Assistant Examiner* — Faye Boosalis
(74) *Attorney, Agent, or Firm* — Andrews Kurth LLP

(57) ABSTRACT

An exemplary apparatus can be provided to determine information regarding a sample(s), which can include, for example an arrangement(s) composed of, at least partially, a particular material in a predetermined area thereof, and including a light facilitating device that can be configured to provide or receive a light radiation(s) to or from the sample(s). The particular material can have a characteristic which can facilitate a sufficient amount of X-ray radiation to pass therethrough so as to generate an X-ray image(s). An X-ray absorption of the material can be at most about 10 times that of a ¼" acrylic plate. The light facilitating device can include a light transmitting configuration which can provide the light radiation(s) to the sample.

21 Claims, 15 Drawing Sheets

(56) References Cited

OTHER PUBLICATIONS

Elmore, G., et al. (1998). "Ten-year risk of false positive screening mammograms and clinical breast examinations." New England Journal of Medicine 338(16): 1089-1096.

Kopans, D. B. (1992). "The Positive Predictive Value of Mammography." American Journal of Roentgenology 158(3): 521-526.

Pisano, E. D., C. Gatsonis, et al. (2005). "Diagnostic Performance of Digital versus Film Mammography for Breast-Cancer Screening." N Engl J Med 353(17): 1773-1783.

ACS (2013). National Cancer Data Base Benchmark Reports. http://www.facs.org/cancer/ncdb/publicaccess.html, American College of Surgeons.

Li, A., E. L. Miller, et al. (2003). "Tomographic optical breast imaging guided by three-dimensional mammography." Applied Optics 42(25): 5181-5190.

Fang, Q., et al. (2009). "Combined Optical Imaging and Mammography of the Healthy Breast: Optical . . . Structure & Compression." Ieee Transactions on Medical Imaging 28(1): 30-42.

Fang, Q., et al. (2011). "Combined optical and X-ray tomosynthesis breast imaging." Radiology 258(1): 89-97.

Gibson, A. P., J. C. Hebden, et al. (2005). "Recent advances in diffuse optical imaging." Physics in Medicine and Biology 50: R1-R43.

Zhang, Q., et al. (2005). "Coregistered tomographic X-ray and optical breast imaging: initial results." Journal of Biomedical Optics 10(2).

Yu, G. Q., et al. (2006). "Real-time in situ monitoring of human prostate photodynamic therapy with diffuse light." Photochemistry and Photobiology 82(5): 1279-1284.

Fletcher, S. W. And J. G. Elmore (2003). "Mammographic screening for breast cancer." New England Journal of Medicine 348(17): 1672-1680.

Rosenberg, RD., et al. (1998). "Effects of age, breast . . . cancer stage at diagnosis: Review of 183,134 screening mammograms in Albuquerque, NM." Radiology 209(2): 511-518.

Kerlikowske, K., et al. (1996). "Effect of age, breast density, and family history on the sensitivity of first screening mammography." JAMA 276(1): 33-38.

Dehghani H, et al. "Structural a priori information in near-infrared optical tomography," Proc. SPIE 6431 (64310B), 2007, pp. 6431001-6431005.

\* cited by examiner

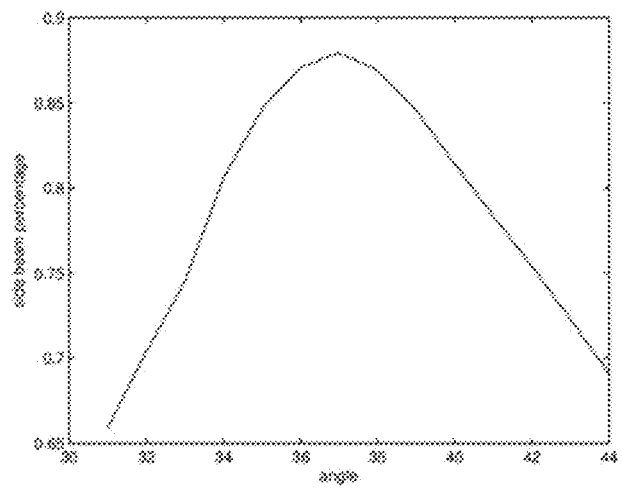

Figure 7A
Plates only
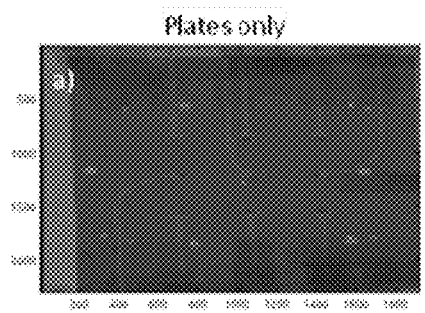
Figure 7B
Eggplant only
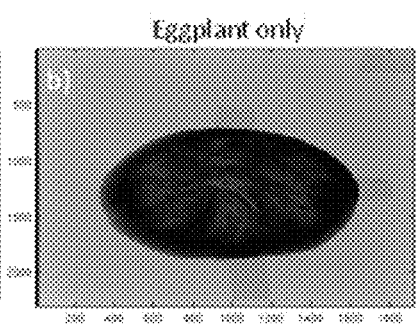
Plates + eggplant
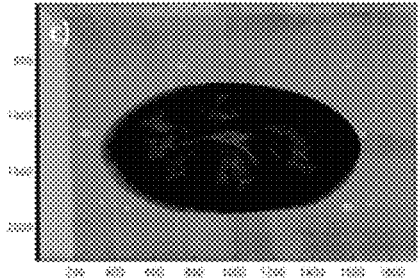
After plate artifact subtraction
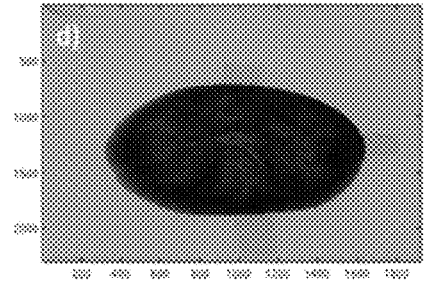
Figure 7C
Figure 7D

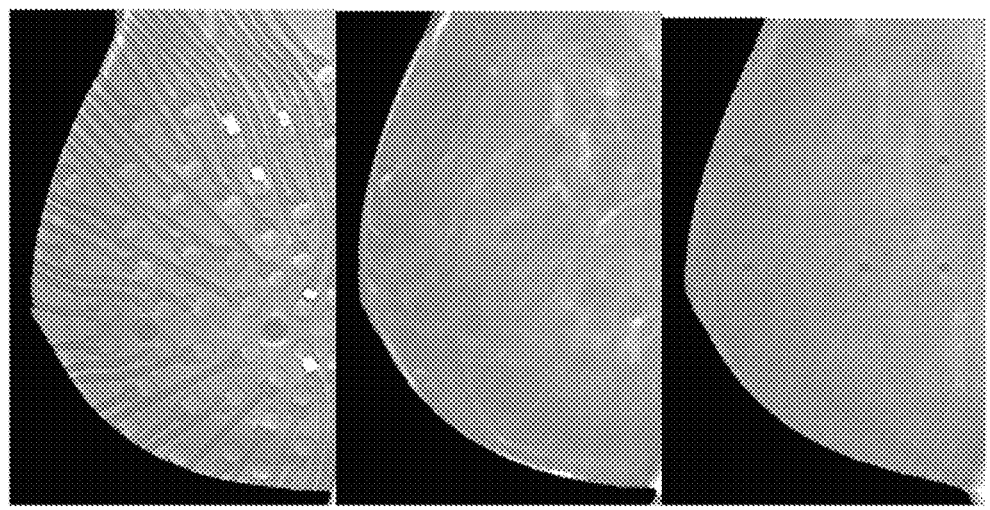

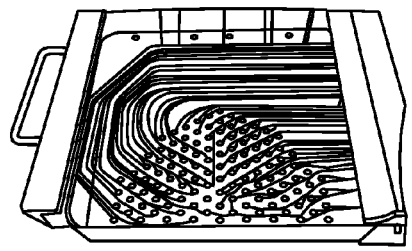 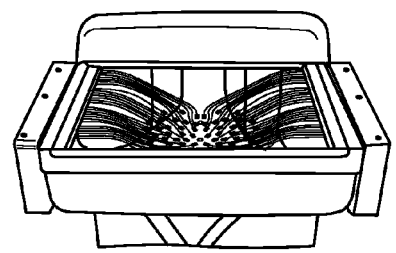
FIG. 12B  FIG. 12C
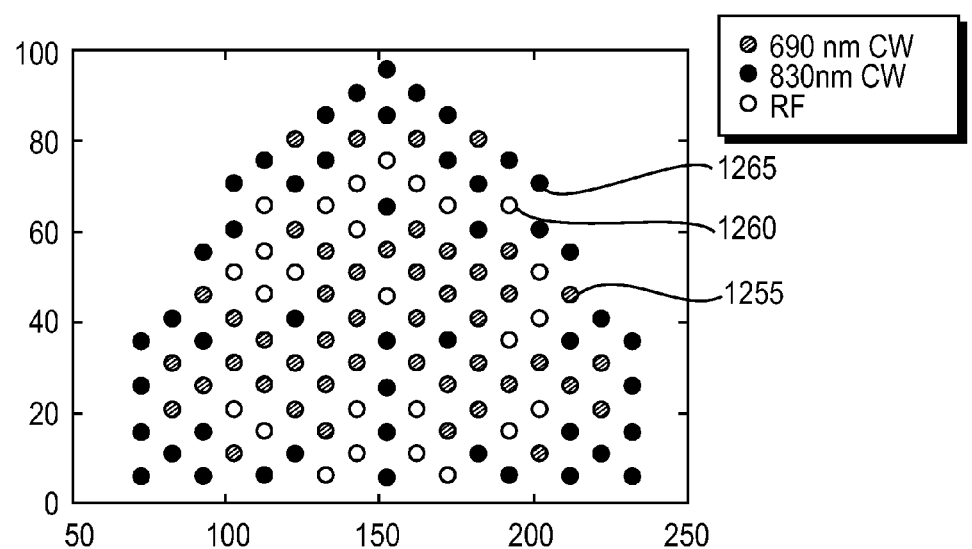
FIG. 12D

OPTICAL FIBER PROBE ARRANGEMENT FOR USE WITH X-RAY MAMMOGRAPHY

CROSS-REFERENCE TO RELATED APPLICATIONS

This application relates to and claims priority from U.S. Patent Application No. 61/892,197, filed on Oct. 17, 2013, the entire disclosure of which is incorporated herein by reference.

FIELD OF THE DISCLOSURE

The present disclosure relates generally to an optical fiber probe, and more specifically, to exemplary embodiments of an exemplary optical fiber probe arrangement for use with X-ray mammography.

BACKGROUND INFORMATION

Breast cancer is still the most common cancer in women worldwide, as well as the primary cause of cancer-related mortality. (See e.g., Reference 1). Advances in mammographic screening, together with new treatment options, have resulted in a shift to earlier stages at initial diagnosis, and a reduction in breast cancer mortality. (See e.g., References 2 and 3). Nevertheless, according to the American Cancer Society, of the approximately over 230,000 women that will be diagnosed with invasive breast cancer in 2014, over 15% of them will die from the disease.

While some tumors can still be discovered by palpation, the majority of breast cancer diagnoses is made with X-ray mammography (see e.g., Reference 4), which can offer greater than 80% sensitivity. (See e.g., References 5 and 6). Still, over 20% of women with breast cancer have had a negative mammogram in the preceding year (see e.g., References 7 and 8), and the specificity can be as low as 20% (e.g., up to an 80% false positive rate). (See e.g., References 9 and 10). Furthermore, the use of mammography has significant difficulties in women with dense breasts (see e.g., Reference 11) and in distinguishing malignant from benign tumors. Therefore, there is a need to detect cancers that may be missed by mammography, and to improve specificity to reduce the number of unnecessary biopsies.

Improved sensitivity and specificity in breast cancer imaging can likely come from multimodal approaches combining structural and functional imaging technologies. Combining low-resolution functional imaging with high-resolution structural imaging in a spatially/temporally co-registered manner can provide a beneficial strategy: for example, utilizing the high-resolution structure images as a prior, the functional imaging modality could yield improved image quality and reduced artifacts (see e.g., References 13 and 15) to deliver more accurate representation of the functional status of tissue. At the same time, certain existing limitations of the structural imaging modalities can be overcome, or reduced, by adding complementary physiological information from the functional imaging modality. Co-registration of the two modalities can also facilitate interpretation of images and the extrapolation of findings from one modality to the other, as well as acceptance by the radiology community of new technologies. (See e.g., Reference 16).

Diffuse optical tomography ("DOT") is an emerging technique that has evolved from transillumination and diaphanography. (See e.g., Reference 18). Facilitated by a preferable low-absorption window of tissue chromophores—e.g., oxy/deoxy-hemoglobin, water and lipids—in the near-infrared ("NIR") range, modern photon detectors can capture NIR signals even after the light has propagated through many centimeters of human tissue, thus providing researchers with a valuable vehicle to probe tissue physiology and metabolism noninvasively. Using certain computer-assisted reconstruction techniques, the researchers can use optical measurements collected from an array of surface sources and detectors to recover tomographic images of deep tissue chromophore maps.

Thus, it may be beneficial to provide exemplary optical fiber probe arrangement for use with X-ray mammography, which can overcome at least some of the deficiencies described herein above.

SUMMARY OF EXEMPLARY EMBODIMENTS

An exemplary apparatus can be provided to determine information regarding a sample(s), which can include, for example an arrangement(s) composed of, at least partially, a particular material in a predetermined area thereof, and including a light facilitating device that can be configured to provide or receive a light radiation(s) to or from the sample(s). The particular material can have a characteristic which can facilitate a sufficient amount of X-ray radiation to pass therethrough so as to generate an X-ray image(s). An X-ray absorption of the material can be at most about 10 times that of a ¼" acrylic plate. The light facilitating device can include a light transmitting configuration which can provide the light radiation(s) to the sample.

In some exemplary embodiments of the present disclosure, the light transmitting configuration can include a waveguide(s). The waveguide can include a plurality of waveguides all located substantially in a same plane. A direction at which the light radiation(s) can be provided can be substantially perpendicular to the plane. The waveguide(s) can include an optical fiber(s). A light blocking arrangement(s) can be located at a distal end of the optical fiber(s) and can be configured to substantially block the light radiation(s) from being provided in all directions except towards the sample(s). The optical fiber(s) can be about 500 microns in size. A direction that the light radiation(s) can be provided can be substantially perpendicular to the predetermined area.

In some exemplary embodiments of the present disclosure, the light facilitating device can include a light receiving configuration which can receive the light radiation(s) from the sample. The light receiving configuration can include a prism(s). The prism(s) can be coupled to a fiber bundle(s). The light facilitating device can includes a light transmitting configuration which can provide the radiation(s) to the sample. The light receiving and transmitting configurations can be provided separately from one another. In the predetermined area, a spatial variation of an X-ray absorption can be substantially uniform. An interface can be provided which can be configured to receive a fiber(s) that can provide the light radiation(s), and can cooperate the light radiation(s) with the light facilitating device to provide the light radiation(s) to the sample(s). An interface can be provided which can be configured to receive a fiber(s) that can receive and forward the light radiation(s) provided from the sample, and cooperate the light radiation(s) with the light facilitating device to forward the light radiation(s) to a photodetector(s).

In certain exemplary embodiments of the present disclosure, the light facilitating device can have a surface(s) that can be provided at an angle that can be between about 10 degrees and about 70 degrees with respect to a direction of the radiation provided from the sample(s). The light facilitating device can be configured to change a direction of the light radiation(s) toward the sample(s). The light facilitating device can also be configured to change a direction of the light radiation(s) provided from the sample(s). A further predetermined area(s) can be configured to partially block the X-ray radiation from passing therethrough.

These and other objects, features and advantages of the exemplary embodiments of the present disclosure will become apparent upon reading the following detailed description of the exemplary embodiments of the present disclosure, when taken in conjunction with the claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 6 is a graph of an exemplary energy percentage in a side firing beam vs. a polish angle in the near optimal angle range according to an exemplary embodiment of the present disclosure;

FIGS. 7A-7D are images of exemplary probe material X-ray artifacts according to an exemplary embodiment of the present disclosure;

FIGS. 11A-11C are images of exemplary breast tomosynthesis slices from a patient according to an exemplary embodiment of the present disclosure;

FIG. 12B is an image of an exemplary source plate according to an exemplary embodiment of the present disclosure;

FIG. 12C is an image of an exemplary detector plate on a digital breast tomosynthesis X-ray detector according to an exemplary embodiment of the present disclosure;

FIG. 12D is a diagram of an exemplary source plate configuration according to an exemplary embodiment of the present disclosure;

Figure 1A:
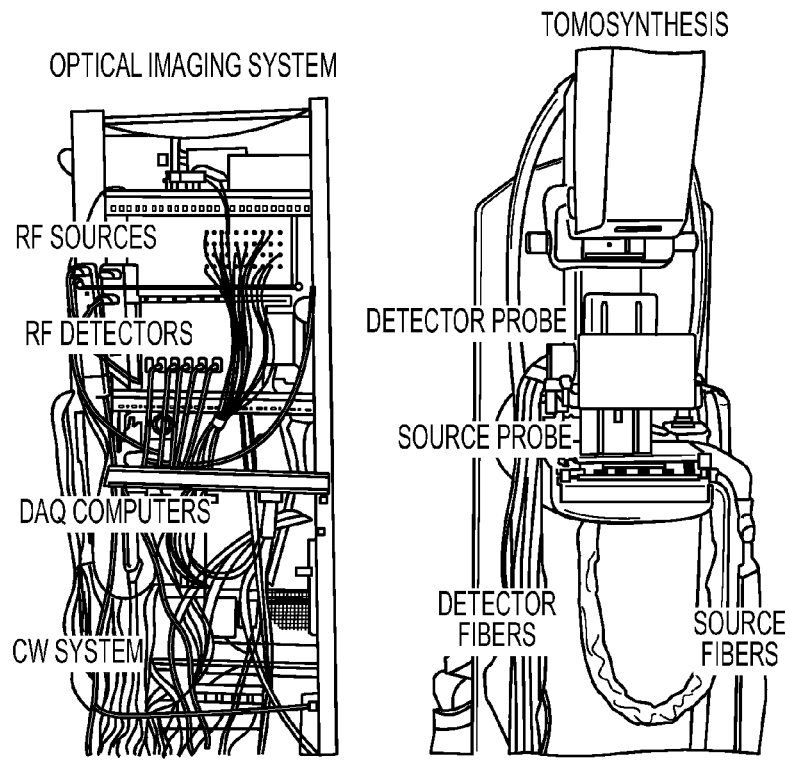
FIG. 1A is an image of an exemplary optical/digital breast tomosynthesis imager according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Combining DOT with X-ray mammography can provide a variety of possible advantages for breast screening and tumor diagnosis. First, the two modalities can be complementary with respect to resolution and diagnostic information. Second, a multi-modality breast imaging system built upon X-ray mammography can rely on its strengths, such as good accessibility and established image interpretations, making it readily available for screening. Furthermore, the incremental manner of adding new diagnostic information to an existing modality can potentially lower the barriers to gaining acceptance from the radiology community.

Figure 1B:
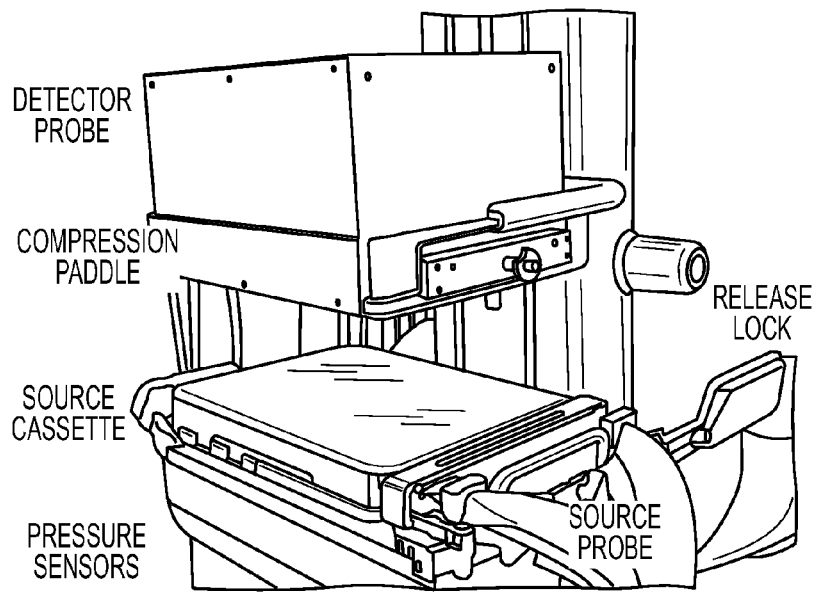
FIG. 1B is an exemplary image of an exemplary optical/digital breast tomosynthesis imager according to an exemplary embodiment of the present disclosure.

A multi-modal breast imaging system combining DOT with digital breast tomosynthesis ("DBT") can be provided. An exemplary tomographic optical breast imager ("TOBI") shown in FIGS. 1A and 1B, was made for producing spatially co-registered optical images when used in conjunction with a 3D DBT system (e.g., GE Healthcare, Gen1.5). TOBI can incorporate state-of-the-art high-speed optical instruments in a tomographic configuration. (See e.g., References 16 and 19). The source module in TOBI can include both continuous-wave ("CW") and radio-frequency ("RF") modulated lasers at about 680 and about 830 nm, and can be capable of imaging tissue scattering in addition to total hemoglobin concentration ("[HbT]") and tissue oxygenation ("$SO_2$").

A study using a combined X-ray/optical imaging system has been conducted. Encouraging preliminary results have been obtained, demonstrating the diagnostic potential of using both X-ray based structural information and optically-derived functional information together in the breast cancer clinical patient management. Using multi-wavelength RF and continuous wave ("CW") measurements from TOBI, and geometric priors from DBT images, researchers performed nonlinear bulk tissue property estimation, and image reconstruction, using a Gauss-Newton approach. The bulk optical properties of the breast tissues are similar to the results from the published literature.

Figure 2A:
FIGS. 2A-2D are images of exemplary breasts imaged using the exemplary apparatus according to an exemplary embodiment of the present disclosure.
Figure 2B:
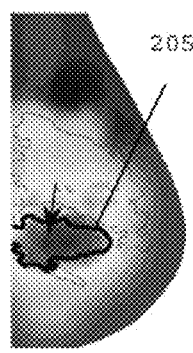
Figure 2C:
Figure 2D:
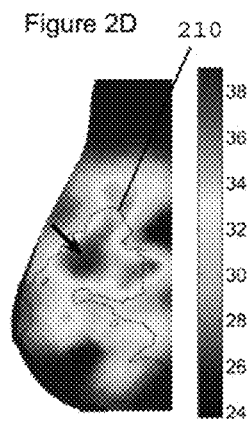

FIGS. 2A and 2B show the exemplary reconstructed image slices for a breast, containing an invasive ductal carcinoma ("IDC") (e.g., in this case, a large portion of the tumor can be ductal carcinoma in situ ("DCIS")). FIGS. 2C and 2D show a further exemplary breast containing an IDC. The corresponding DBT image slice, the contours of the tumor (e.g., element 205) and the fibroglandular tissue (e.g., element 210) are also shown in FIGS. 2B and 2D, respectively. The exemplary [HbT] image of the lesion-bearing breast in FIG. 2B presents a positive contrast (e.g., about 2:1) with margins well fitted within the contours of the lesion. The scattering coefficient image shows a similar pattern. The $SO_2$ values inside the tumor region demonstrate a slightly lower value compared with the surrounding tissue. These exemplary findings are similar to published signatures of malignant lesions such as high vessel density and high metabolism. (See e.g., Reference 17).

While the exemplary TOBI/DBT examination can be performed fairly quickly (e.g., data acquisition less than about 2 minutes), the use of metal in the construction of the exemplary optical plates can benefit from separating the optical from the X-ray exam by manually removing the optical plates after the 45 second optical image. The patient can remain under compression during this time, leading to unneeded discomfort. A significant reduction in the procedure time and patient compression duration can be achieved by fabricating optical probes from an X-ray translucent material, facilitating true simultaneous dual-modality imaging. Plates containing the optical fibers can be built from acrylic sheets or another suitable X-ray translucent material. These plates can be mated to the exemplary X-ray device breast compression plate and X-ray detector, respectively, using suitable means of retainment. The area to be covered by light, other energy emission or capture locations can be determined from histograms of compressed breast geometries from previous clinical measurements, breast morphometry studies, or any other suitable survey of breast dimensions.

The exemplary optical probes can be based on maximum optical efficiency and minimized X-ray image disruption. Table 1 below details exemplary measurements acquired of X-ray absorption properties of the different materials that can be used in probe fabrication, together with the properties of a typical mammography phantom (e.g., Gammex 156) used for instrument quality control as a reference. The majority of these exemplary materials may only absorb a small fraction of X-ray photons compared to a typical breast. Glass optical fiber bundles, often used for light capture for optical imaging, can have excessive X-ray absorption, highlighting the need to use a more X-ray translucent material, such as plastic optical fibers ("POF") for the detectors. The recent development of perfluorinated materials for POFs has greatly improved optical transmission properties compared to the older PMMA (e.g., acrylic) POFs, with attenuation as low as 0.06 dB/m throughout the NIR range.

Minimizing the thickness of the probe components can be essential to reduce X-ray artifacts. An exemplary design can have optical fibers/bundles enter from the side, and can either be embedded in a plastic plate, or sandwiched between two plastic plates. Glass or plastic fibers can be used for the sources, while large diameters plastic fibers can be a good choice for collecting light transmitted through the tissue. Several exemplary designs with various tradeoffs between complexity and X-ray absorption can include the following:

Straight optical fibers can terminate in an about 10-70 degree side cut, for example an about 45 degree side cut. (See e.g., Reference 19). Both incoming and tissue transmitted light can undergo total internal reflection at the inclined fiber/air interface. Therefore, no additional light reflecting components can be needed. This exemplary design can minimize probe thickness, but losses of approximately 20% or more can be expected compared to front facing fibers.

Straight optical fibers can terminate at a glass, plastic or other radiation bending material microprism (e.g., matching source and detector waveguide size) that can reflect and collect light into/out of the tissue. This exemplary design can offer provide superior light efficiency, but the prism material should be selected to minimize the impact on X-ray image reconstruction.

Tightly bent 5-400 μm optical fibers (e.g., source plate) and 1-5 mm fiber bundles (e.g., detection side) can be used. This can be a simple design, but can suffer from potential bending related light loss, and a substantial fiber material component along the X-ray axis.

Figure 3:
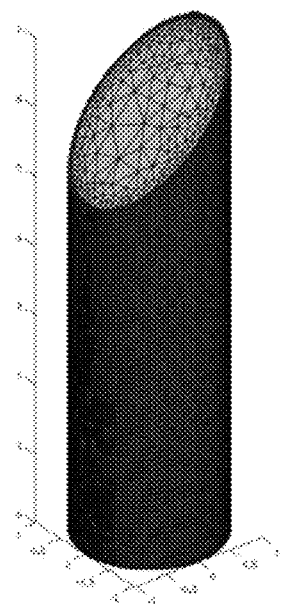
FIG. 3 is a diagram of a three-dimensional mesh used to simulate light from a side cut optical waveguide according to an exemplary embodiment of the present disclosure.

Side fiber cut angle optimization can be performed using analytical or numerical modeling. For example, a 3D mesh generator (e.g., the iso2 mesh package) was used to create 3D tetrahedral meshes to accurately model the geometry of a side-firing fiber. (See FIG. 3). The tetrahedral mesh model can contain both the core and cladding regions of a fiber, with an adjustable outer/inner radius and top-face tilting angle (e.g., α, relative to the axis of the fiber). This exemplary mesh model can be used to accurately simulate light propagation from various optical fiber structures, including both step-indexed and graded index fibers.

Figure 4:
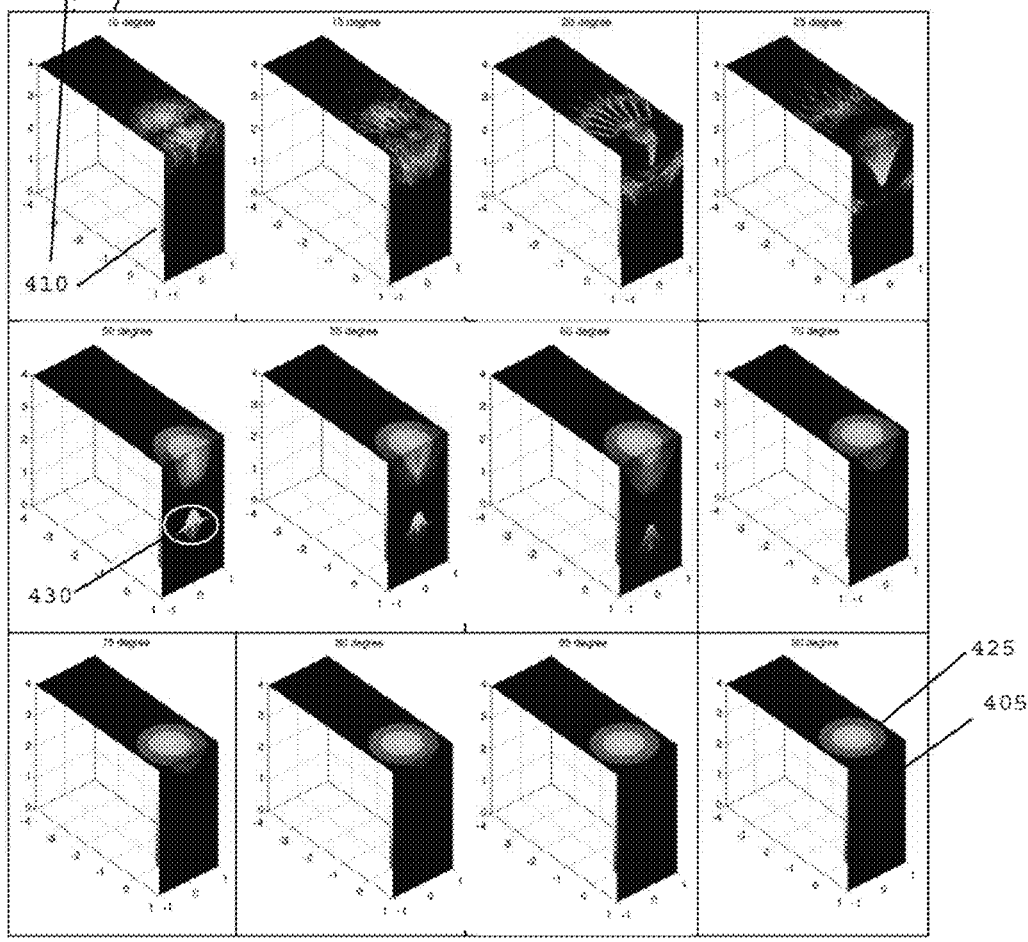
FIG. 4 is a set of exemplary emission patterns using the simulation geometry from FIG. 3 according to an exemplary embodiment of the present disclosure.

FIG. 4 shows the front (element 425) and side-firing (element 405) output from an angle polished fiber 410 with a polish angle 415 with respect to the fiber direction. A maximum power in the side-firing area 430 can be beneficial, and the light emission distribution over multiple polish angles over a range of the polish angle 415 from about 10 to about 90 degrees is demonstrated.

Figure 5:
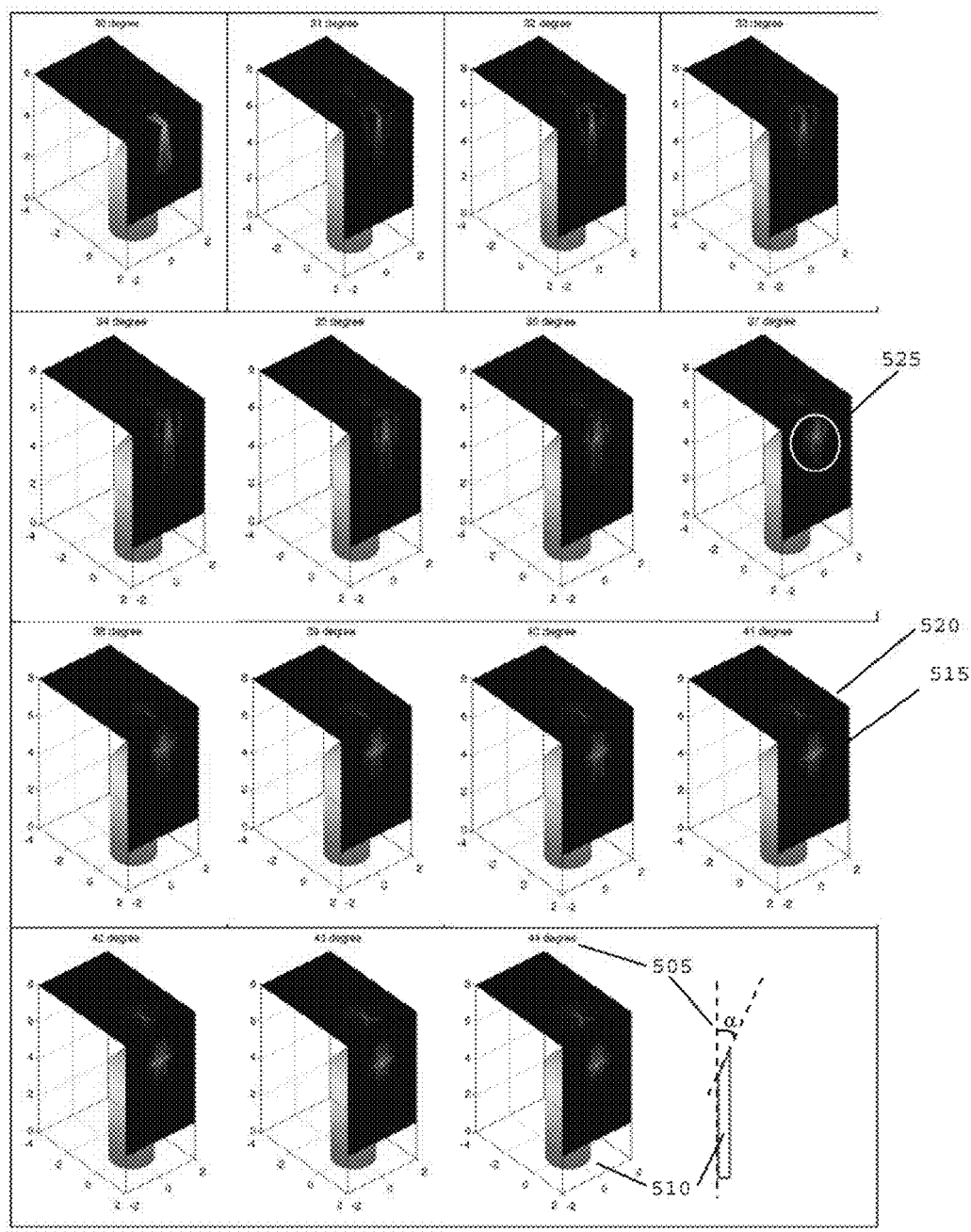
FIG. 5 is a set of exemplary emission patterns displayed for a narrow range of side cut angles near the optimal angular value according to an exemplary embodiment of the present disclosure.

FIG. 5 shows the front (element 520) and side-firing (element 515) output from an angle polished fiber 510 with a polish angle 505 with respect to the fiber direction. A maximum power in the side-firing area 525 and the light emission distribution over multiple polish angles over a range of the polish angle 505 between about 30 and about 44 degrees is demonstrated.

FIG. 6 shows a plot of the percentage of the total output energy emitted through the side-firing beam (element 525 from FIG. 5) as a function of the polish angle of the fiber (element 505 from FIG. 5).

A substantially accurate photon transport simulation procedure was developed using an exemplary Monte Carlo procedure and a tetrahedral mesh. The exemplary procedure can be called a "mesh-based Monte Carlo", or MMC. Using this exemplary procedure, photons propagating inside a complex domain, such as the side cut fiber model shown in FIG. 3, can be simulated, and the light emission profile at the tip of the fiber can be calculated.

Using the parameters for one of the commercially available optical fibers, an exemplary 3D fiber model was created, a series of MMC simulations can be run, and the light transmission profiles for a range of tilting angle (α) of a side-firing fiber can be obtained. The light transmission profiles corresponding to α ranging from 10 degree to 90 degree are shown in Table 1 below.

TABLE 1

X-ray absorption density of various probe related materials

| Material | X-ray Density ($-\log (I/I_0)$) | Percentage of breast phantom |
| --- | --- | --- |
| Mammography Breast Phantom (Gammex 156) | 1.12 | 100% |
| 400 micron glass fiber | 0.09 | 8% |
| 3 mm plastic fiber | 0.08 | 7% |

TABLE 1-continued

X-ray absorption density of various probe related materials

| Material | X-ray Density ($-\log (I/I_0)$) | Percentage of breast phantom |
| --- | --- | --- |
| 2.5 mm glass fiber bundle | 1.02 | 91% |
| ¼" acrylic plate | 0.18 | 16% |

From the light distributions on the top- and side-panels, the emergence and fading of a side beam can be evident, especially when $10<\alpha<50$. A fine-grained set of simulations can be performed to find the optimal polish angle. Specifically, the energy transmission ratios between the side-firing beam and the total incident energy can be calculated and the maximum can be sought.

For this exemplary fiber configuration (e.g., core/cladding diameter, refractive indices), an exemplary tilting angle can be about 37 degree. At this angle, about 88% of the light energy can transmit through the side-firing beam. This exemplary simulation can be applied for any other fiber configurations to optimize the tilting angle for a side-firing optical fiber.

Even X-ray translucent materials can leave a certain amount of artifacts in the X-ray image, for example, the breast mammogram or breast 3D digital breast tomosynthesis volume. Artifact removal can be accomplished at many levels, for example, by reference subtraction from the raw X-ray projections, by pattern recognition and removal, or by 3D reconstruction algorithms that can localize the artifacts substantially away from the breast tissue.

Using several exemplary test targets, probe artifacts can be removed from the X-ray images by first acquiring the probe X-ray shadow, and then aligning and subtracting it from the combined X-ray image. FIGS. 7A-7D illustrate exemplary images where a 5 cm thick slice of eggplant was placed on top of a prototype detector plate that included PMMA fibers and prisms. The plate and the eggplant were sandwiched between the X-ray detector and the compression plate of the exemplary tomosynthesis machine. FIG. 7A shows the X-ray shadow of the prototype detector plate (e.g., contrast enhanced for visibility), while FIG. 7B shows an X-ray of the eggplant slice. FIG. 7C shows the X-ray of the eggplant and plate combination, and FIG. 7D shows the results of aligning and subtracting the probe shadow in FIG. 7A from the X-ray image in FIG. 7C. The artifact removal appears is beneficial.

In an exemplary embodiment according to the present disclosure, the source laser diodes can be coupled to a standard approximately 500 micron glass fiber, which can then be coupled into an approximately 500 micron PMMA fiber that can enter the source plate. The fiber can terminate at about a 36 degree angle cut, which can be optimized for side firing, and the tip can be embedded in about a 4 mm black plastic button that can absorb stray light. A total of about 120 fibers can be built into a polycarbonate plate about ⅛" thick, which can be attached under the mammography machine compression paddle. Both glass and plastic fiber diameters can vary as needed (e.g., can be as small as 50 microns, and as large as 1-2 mm if routing can be achieved). The angle cut can be optimized numerically for each fiber type. The stray light blocking termination can take any shape that can enclose the fiber tip.

In another exemplary embodiment, after passing through the breast, the light or other electro-magnetic radiation can be collected by a plastic prism that can send it into about a 2 mm solid PMMA fiber. Finally, after the PMMA fiber exits the plate, the light or other electro-magnetic radiation can be coupled to about a 2.5 mm glass fiber bundle that can carry it to the photodetectors. By using the side firing angle polish and the collection prisms, the entire fiber assembly can be flat, and can be embedded in about a ¼" thick polycarbonate plate, the same material used for the X-ray compression paddles. A total of about 54 detector fibers can be built into the plate, meant to be attached above the X-ray machine detector cover.

Figure 8:
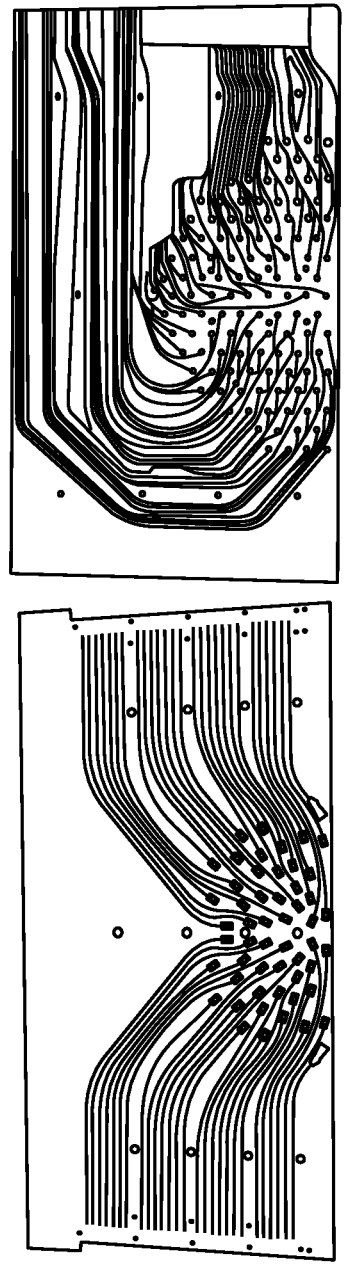
FIG. 8 is a set of images of an exemplary light emission fiber holder, and an exemplary light collection fiber holder, according to an exemplary embodiment of the present disclosure.

Using several exemplary devices with increasing numbers of embedded optical components, CAD drawing for each element, as well as the CNC machining parameters can be optimized. Exemplary patterns can be used to place the about 120 source and about 54 detection channels, and the exemplary plastic probe plates can be fabricated that can hold the exemplary optical components described above. FIG. 8 shows exemplary photographs of the exemplary plates ready for final assembly.

Figure 9:
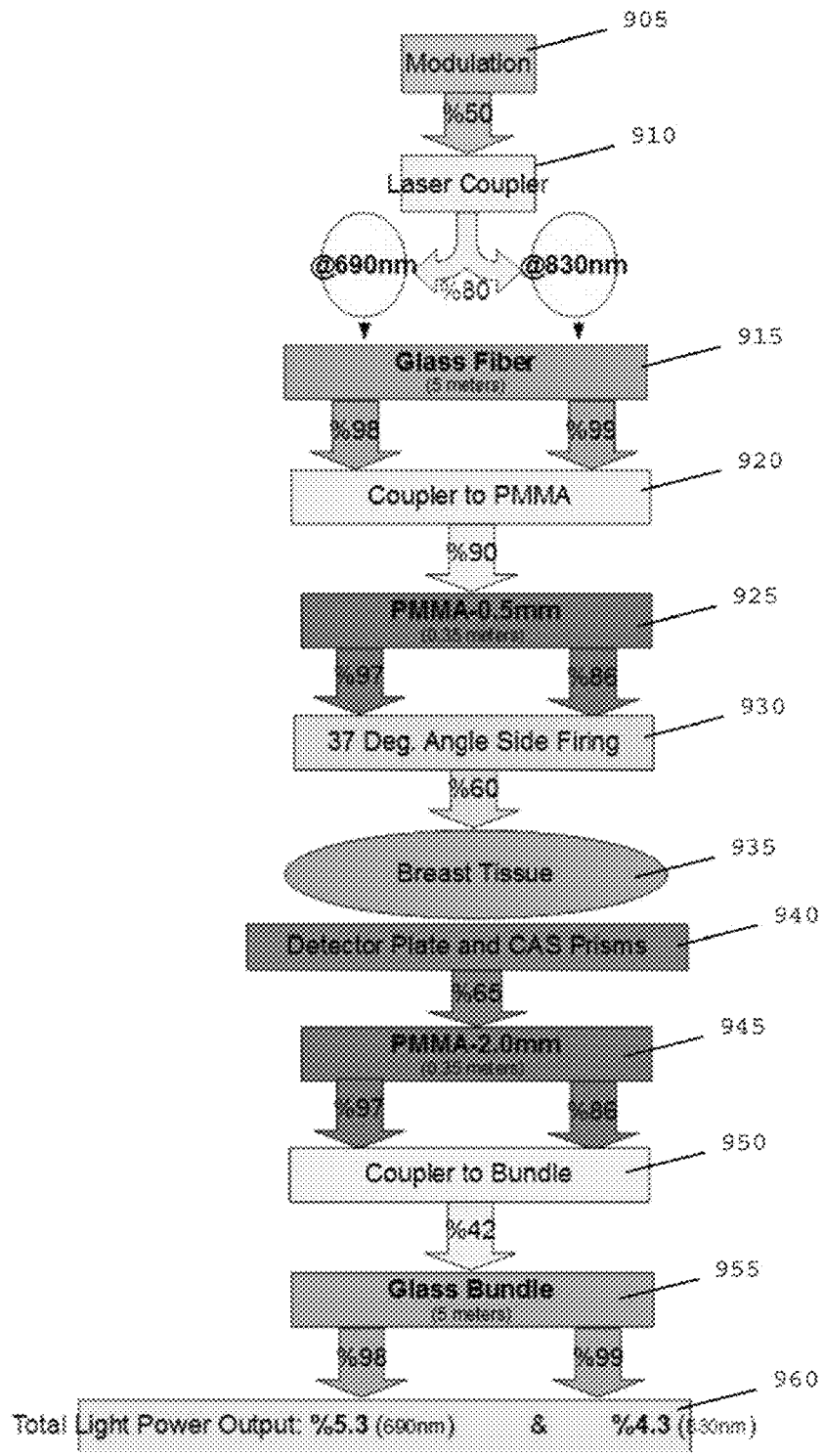
FIG. 9 is a diagram of an exemplary light budget analysis procedure according to an exemplary embodiment of the present disclosure.

FIG. 9 illustrates a schematic description of the exemplary light transmission characteristics according to an exemplary embodiment of the present disclosure. The exemplary embodiment can include a unit source power (e.g., a laser diode), which can modulated with a square wave (905). The modulated light from the light source can then be coupled using a laser to fiber coupler 910 into a glass optical fiber 915 (e.g., an approximately 500 micron core optical fiber). The light output from 915 can be further coupled using a fiber to fiber coupler 920 to a PMMA plastic fiber 925, which can be terminated with about a 37 degree angle polish 930 for side firing into the sample (e.g., breast tissue 935). Light re-emitted from the tissue 935 can be captured by plastic prisms 940 that can couple the light to an about 2.0 mm PMMA fiber(s) 945. The output of the PMMA fiber(s) 945 can be coupled to glass fiber bundles 955 using a fiber to fiber coupler 950. The total light transmission 960 can be estimated for light of about 690 nm and about 830 nm assuming about 5 meter long glass fiber elements 915 and 955, and about 0.35 meter long plastic fiber elements 925 and 955, and employing previously determined transmission and coupling efficiencies for each wavelength at each step of the transmission path.

Figure 10B:
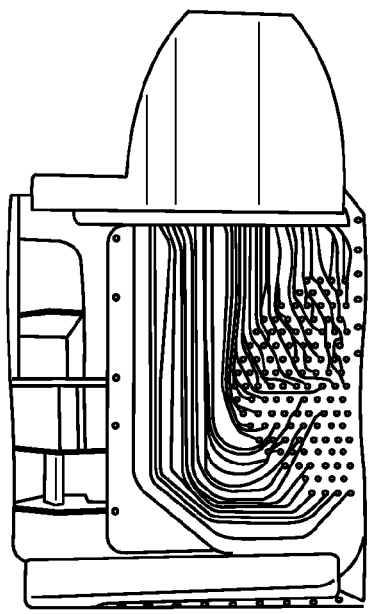
FIGS. 10A and 10B are exemplary images of exemplary assembled detectors and sources according to an exemplary embodiment of the present disclosure.
Figure 10A:
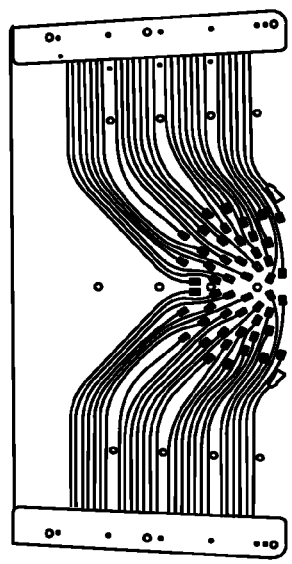

FIGS. 10A and 10B show two exemplary embodiments of the present disclosure with light guiding elements and stiffening and protection features. FIG. 10A shows an exemplary light collection probe with plastic prisms that can redirect light from the sample into thick plastic optical fibers that follow a curvilinear path to a coupling zone near the edge of the holder. Where the light is transitioned to glass fiber bundles, the transition area is protected with a rigid enclosure that can also serve as flush mounting means to a Hologic Selenia DBT X-ray detector cover. FIG. 10B shows an exemplary light emission probe design where glass fibers come in from the instrumentation, mate with plastic fibers at the edge in protected channels, and the light is delivered at the inner end of the plastic fibers through internal reflection due to the angle polish. The plastic light delivery fibers can be terminated in black plastic holders to avoid stray light emission (e.g., from a front firing light). A metal plate can shield the fiber coupling region, and the entire plate can be rigidly mated to a standard commercial breast compression plate using a shaped plastic mounting system with screw attachments.

FIGS. 11A-11C are exemplary images of breast tomosynthesis slices from an actual patients showing the X-ray shadow pattern at the detector plate (FIG. 11A), at the source plate (FIG. 11C) and the nearly complete removal of artifacts achieved by the commercial DBT image reconstruction software mid-way within the breast (FIG. 11B).

Figure 12A:
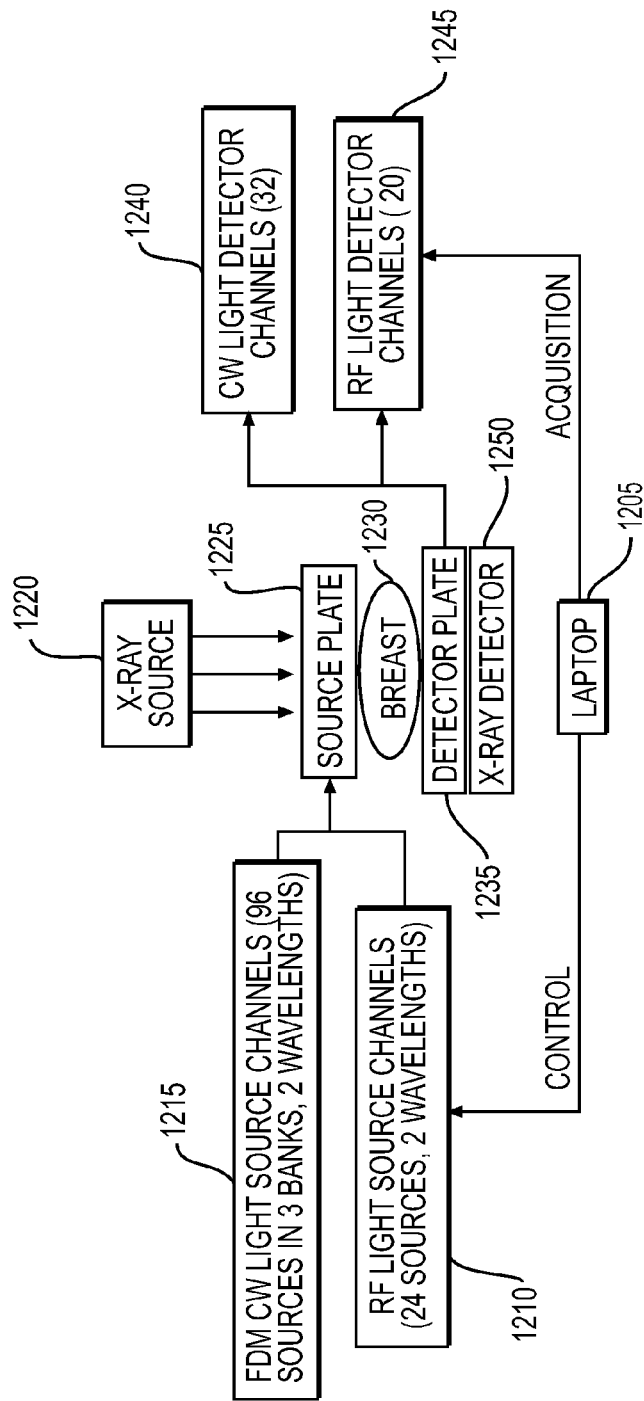
FIG. 12A is a diagram of an exemplary system according to an exemplary embodiment of the present disclosure.

FIG. 12A illustrates a system diagram for an exemplary diffuse optical tomography system. A computer (e.g., laptop 205) can control one or more RF light source channels 1210, which can include 24 sources and 2 wavelengths. Laptop 205 can also control FDM CW light source channels, which can include 96 sources in 3 blanks, and 2 wavelengths. The output of the RF light source channels and the FDM CW light source channels can be input into a source plate 1225, which can also include X-rays from X-ray source 1220. The light radiation and the X-ray radiation can be provided to tissue (e.g., breast 1225), in conjunction with an X-ray detector 1250 and RF light detector channels 1245 and CW light detector channels 1240, and the source plate and detector plate in this diagram)

Figure 12E:
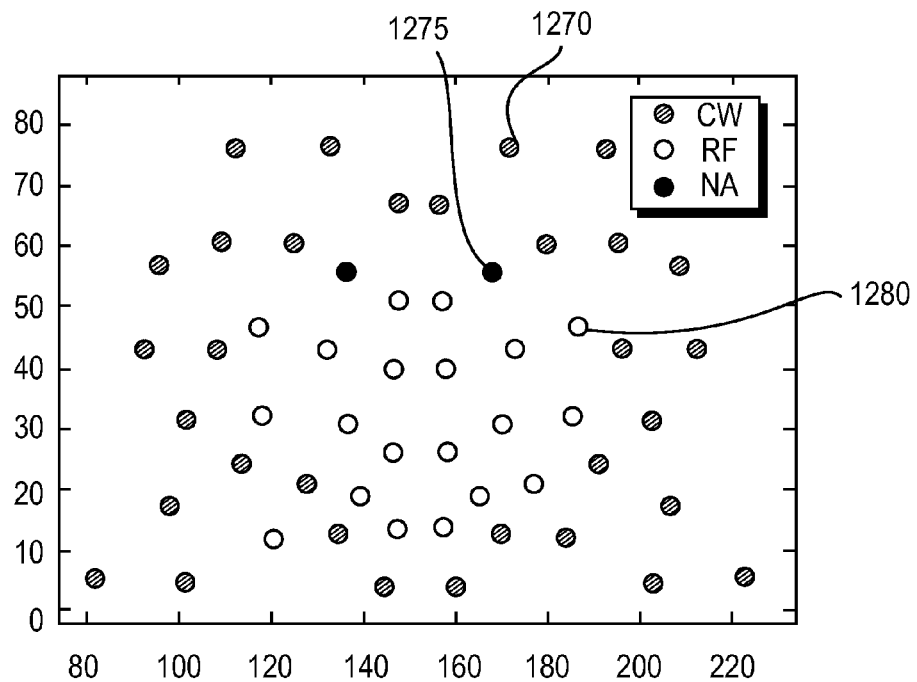
FIG. 12E is a diagram of an exemplary detector plate configuration according to an exemplary embodiment of the present disclosure.

FIG. 12B shows a photograph of the source (e.g., light emission) plate mounted on a standard size Hologic breast compression paddle compatible with a Hologic Selenia Dimensions mammography/tomosynthesis system. FIG. 12C shows a photograph of the detector (e.g., light collection) plate mounted on the X-ray detector cover Hologic Selenia Dimensions mammography/tomosynthesis system. FIG. 12D shows an exemplary assignment of light emission locations to the signal source components of the exemplary DOT system/apparatus system having a continuous wave light at 690 nm (e.g., element 1255) and at 830 nm (e.g., element 1260), and radio frequency modulated light (e.g., element 1265) of mixed 690 and 830 wavelengths. FIG. 12E shows an exemplary assignment of light collection locations to the exemplary photodetection components of the exemplary DOT system/apparatus with CW photodetectors 1270, RF photodetectors 1280, not assigned spaces 1275).

Figure 12F:
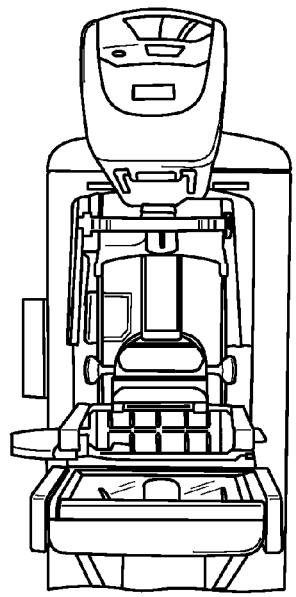
FIG. 12F is an image of an exemplary optical probe on a digital breast tomosynthesis machine according to an exemplary embodiment of the present disclosure.
Figure 12G:
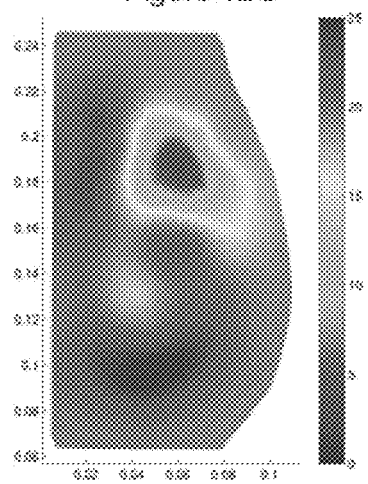
FIG. 12G is an exemplary image generated by an absolute HbT reconstruction according to an exemplary embodiment of the present disclosure.
Figure 12H:
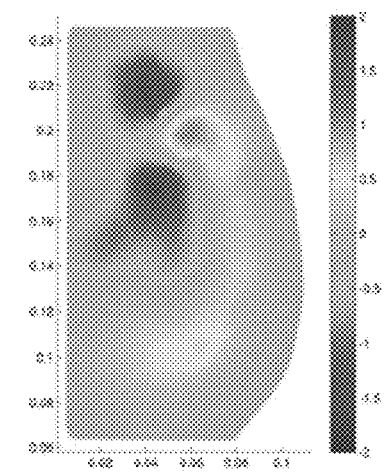
FIG. 12H is an exemplary image of changes in HbT due to breast compression at time t after compression is applied, where t equals 30 s according to an exemplary embodiment of the present disclosure.
Figure 12I:
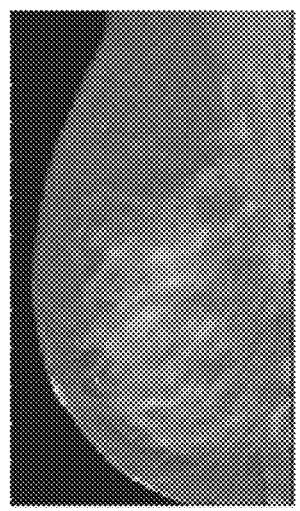
FIG. 12I is an image of a digital breast tomosynthesis slice according to an exemplary embodiment of the present disclosure.

FIG. 12F shows an exemplary source and detector plate mounted on a Hologic Selenia Dimensions X-ray mammography/tomosynthesis system. FIG. 12G shows an exemplary reconstruction of total hemoglobin concentration in units of micromoles per liter in an adult human volunteer imaged with the exemplary system/apparatus shown in FIG. 12A. FIG. 12H shows an exemplary reconstruction of compression induced changes in total hemoglobin concentration in units of micromoles per liter in an adult human volunteer imaged with the exemplary system/apparatus of FIG. 12A at 30 seconds after the breast compression is complete. FIG. 12I shows a mid-height slice of the exemplary X-ray digital breast tomosynthesis reconstruction of the subject's breast (corresponding to the images in FIGS. 12G and 12H).

Using several test targets, probe artifacts from the X-ray images can be removed by acquiring the probe X-ray shadow, and then aligning and subtracting it from the combined X-ray image. FIGS. 7A-7D shows an example where a 5 cm thick slice of eggplant was placed on top of a prototype detector plate that included PMMA fibers and prisms. The plate and the eggplant were sandwiched between the X-ray detector and the compression plate of the exemplary tomosynthesis machine. FIG. 7A shows the X-ray shadow of the exemplary detector plate (e.g., contrast enhanced for visibility), while FIG. 7B shows an X-ray of the eggplant slice. FIG. 7C shows the X-ray of the eggplant and plate combination while FIG. 7D shows the results of aligning and subtracting the probe shadow in FIG. 7A from the X-ray image in FIG. 7C. The artifact removal appears to be excellent.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] GLOBOCAN2008. "Estimated cancer Incidence, Mortality, Prevalence and Disability-adjusted life years (DALYs) Worldwide in 2008." Retrieved Oct. 1, 2013, from http://globocan.iarc.fr/.

[2] Berry, D. A., Cronin, K. A., Plevritis, S. K., Fryback, D. G., Clarke, L., Zelen, M., Mandelblatt, J. S., Yakovlev, A. Y., Habbema, J. D. and Feuer, E. J. (2005). "Effect of screening and adjuvant therapy on mortality from breast cancer." The New England journal of medicine 353(17): 1784-1792.

[3] Chatterjee, Neal A., He, Yulei and Keating, Nancy L. (2012). "Racial Differences in Breast Cancer Stage at Diagnosis in the Mammography Era." American Journal of Public Health 103(1): 170-176.

[4] Singletary, S. E. (2007). "Multidisciplinary frontiers in breast cancer management—A surgeon's perspective." Cancer 109(6): 1019-1029.

[5] Kerlikowske, K., D. Grady, et al. (1996). "Effect of age, breast density, and family history on the sensitivity of first screening mammography." Jama-Journal of the American Medical Association 276(1): 33-38.

[6] Rosenberg, R. D., W. C. Hunt, et al. (1998). "Effects of age, breast density, ethnicity, and estrogen replacement therapy on screening mammographic sensitivity and cancer stage at diagnosis: Review of 183,134 screening mammograms in Albuquerque, N. Mex." Radiology 209(2): 511-518.

[7] Elmore, G., M. B. Barton, et al. (1998). "Ten-year risk of false positive screening mammograms and clinical breast examinations." New England Journal of Medicine 338(16): 1089-1096.

[8] Fletcher, S. W. and J. G. Elmore (2003). "Mammographic screening for breast cancer." New England Journal of Medicine 348(17): 1672-1680.

[9] Kopans, D. B. (1992). "THE POSITIVE PREDICTIVE VALUE OF MAMMOGRAPHY." American Journal of Roentgenology 158(3): 521-526.

[10] Mendez, A., F. Cabanillas, et al. (2004). "Mammographic features and correlation with biopsy findings using 11-gauge stereotactic vacuum-assisted breast biopsy (SV-ABB)." Annals of Oncology 15(3): 450-454.

[11] Pisano, E. D., C. Gatsonis, et al. (2005). "Diagnostic Performance of Digital versus Film Mammography for Breast-Cancer Screening." N Engl J Med 353(17): 1773-1783.

[12] ACS (2013). National Cancer Data Base Benchmark Reports. http://www.facs.org/cancer/ncdb/publicaccess.html, American College of Surgeons.

[13] Li, A., E. L. Miller, et al. (2003). "Tomographic optical breast imaging guided by three-dimensional mammography." Applied Optics 42(25): 5181-5190.

[14] Dehghani H, C. M. Carpenter, R. K. Yalavarthy, B. W. Pogue and J. P. Culver, "Structural a priori information in near-infrared optical tomography," Proc. SPIE 6431 (64310B), 2007, pp. 6431001-6431005

[15] Fang, Q., S. A. Carp, et al. (2009a). "Combined Optical Imaging and Mammography of the Healthy Breast: Optical Contrast Derived From Breast Structure and Compression." Ieee Transactions on Medical Imaging 28(1): 30-42.

[16] Fang, Q., Selb, J., Carp, S. A., Boverman, G., Miller, E. L., Brooks, D. H., Moore, R. H., Kopans, D. B. and Boas, D. A. (2011). "Combined optical and X-ray tomosynthesis breast imaging." Radiology 258(1): 89-97.

[17] Gibson, A. P., J. C. Hebden, et al. (2005). "Recent advances in diffuse optical imaging." Physics in Medicine and Biology 50: R1-R43.

[18] Zhang, Q., T. J. Brukilacchio, et al. (2005). "Coregistered tomographic X-ray and optical breast imaging: initial results." Journal of Biomedical Optics 10(2).

[19] Yu, G. Q., T. Durduran, et al. (2006). "Real-time in situ monitoring of human prostate photodynamic therapy with diffuse light." Photochemistry and Photobiology 82(5): 1279-1284.

What is claimed is:

1. An apparatus to determine information regarding at least one sample, comprising:
at least one arrangement composed of, at least partially, a particular material in a predetermined area thereof, and including a light facilitating device that is configured to at least one of provide or receive at least one light radiation to or from the at least one sample,
wherein the particular material has (i) a characteristic which facilitates a sufficient amount of X-ray radiation to pass therethrough so as to generate at least one X-ray image and (ii) an X-ray absorption, which is at most about 10 times that of a ¼" acrylic plate.

2. The apparatus according to claim 1, wherein the light facilitating device includes a light transmitting configuration which provides the at least one light radiation to the at least one sample.

3. The apparatus according to claim 2, wherein the light transmitting configuration includes at least one waveguide.

4. The apparatus according to claim 3, wherein the at least one waveguide includes a plurality of waveguides all located substantially in a same plane.

5. The apparatus according to claim 4, wherein a direction at which the at least one light radiation is provided is substantially perpendicular to the plane.

6. The apparatus according to claim 3, wherein the at least one waveguide includes at least one optical fiber.

7. The apparatus according to claim 6, further comprising at least one light blocking arrangement located at a distal end of the at least one optical fiber configured to substantially block the at least one light radiation from being provided in all directions except towards the at least one sample.

8. The apparatus according to claim 6, wherein the at least one optical fiber is about 500 microns in size.

9. The apparatus according to claim 1, wherein a direction that the at least one light radiation is provided is substantially perpendicular to the predetermined area.

10. The apparatus according to claim 1, wherein the light facilitating device includes a light receiving configuration which receives the at least one light radiation from the at least one sample.

11. The apparatus according to claim 10, wherein the light receiving configuration includes at least one prism.

12. The apparatus according to claim 11, wherein the at least one prism is coupled to at least one fiber bundle.

13. The apparatus according to claim 10, wherein the light facilitating device further includes a light transmitting configuration which provides the at least one light radiation to the at least one sample.

14. The apparatus according to claim 13, wherein the light receiving and transmitting configurations are provided separately from one another.

15. The apparatus according to claim 1, wherein in the predetermined area, a spatial variation of the X-ray absorption is substantially uniform.

16. The apparatus according to claim 1, further comprising an interface which is configured to receive at least one fiber that provides the at least one light radiation, and cooperate the at least one light radiation with the light facilitating device to provide the at least one light radiation to the at least one sample.

17. The apparatus according to claim 1, further comprising an interface which is configured to receive at least one fiber that receives and forwards the at least one light radiation provided from the at least one sample, and cooperate the at least one light radiation with the light facilitating device to forward the at least one light radiation to at least one photodetector.

18. The apparatus according to claim 1, wherein the light facilitating device has at least one surface that is provided at an angle that is between about 10 degrees and about 70 degrees with respect to a direction of the light radiation provided from the at least one sample.

19. The apparatus according to claim 1, wherein the light facilitating device is configured to change a direction of the at least one light radiation toward the at least one sample.

20. The apparatus according to claim 1, wherein the light facilitating device is configured to change a direction of the at least one light radiation provided from the at least one sample.

21. The apparatus according to claim 1, further comprising at least one further predetermined area configured to partially block the X-ray radiation from passing therethrough.

* * * * *